United States Patent [19]

Giampapa

[11] Patent Number: 4,888,018
[45] Date of Patent: Dec. 19, 1989

[54] METHOD OF POSITIONING AND SECURING A CHIN IMPLANT

[76] Inventor: Vincent C. Giampapa, 67 Highland Ave., Montclair, N.J. 07043

[21] Appl. No.: 290,711

[22] Filed: Dec. 27, 1988

[51] Int. Cl.$^4$ .............................................. A61F 2/28
[52] U.S. Cl. ..................................................... 623/16
[58] Field of Search ...................... 623/11, 13, 16, 18; 433/173, 174

[56] References Cited

U.S. PATENT DOCUMENTS

| D. 290,879 | 7/1987 | Giampapa et al. | 623/16 |
|---|---|---|---|
| 3,178,728 | 4/1965 | Christensen | 623/11 |
| 3,720,959 | 3/1973 | Hahn | 623/16 |
| 3,745,995 | 7/1973 | Kraus | 623/16 |
| 3,790,507 | 2/1974 | Hodosh | 623/16 |
| 3,849,805 | 11/1974 | Leake et al. | 623/16 |
| 4,344,191 | 8/1982 | Wagner | 623/16 |
| 4,439,152 | 3/1984 | Small | 433/173 |

FOREIGN PATENT DOCUMENTS

| 2447182 | 9/1980 | France | 623/11 |
|---|---|---|---|
| 0637118 | 12/1978 | U.S.S.R. | 623/16 |

Primary Examiner—Richard J. Apley
Assistant Examiner—David J. Isabella
Attorney, Agent, or Firm—Melvin K. Silverman

[57] ABSTRACT

A method of applying a chin implant to a human, the method including the steps of positioning a resilient preformed chin implant against an area of the chin to be enhanced, the implant having an interior radius having a curvature slightly smaller than the opposing radius of the curvature of the area of the chin which is to receive the implant. As a second step, a mounting pin bore is drilled through the implant and into the periostium of the area of the chin at an outward angulation of about thirty degrees relative to a front-to-rear vertical medial plane of the face and, concurrently, at a downward angulation of about thirty degrees relative to a front-to-horizontal plane of the face taken through the area of the chin to be enhanced. A third step is defined by drilling through the implant and into the periostium a mounting pin bore having, about the front-to-rear vertical median plane, a mirror symmetry to the drilled hole described above. As a final step, there is securably inserted, through the bores, respective mounting pins which penetrate into the periostium to a depth of between two and five millimeters. Due to the difference in the radii of curvature of the inner surface of the implant and the opposing area of the chin, the two mounting pins will secure the implant at a substantially crescent-shaped offset from the chin.

7 Claims, 1 Drawing Sheet

U.S. Patent
Dec. 19, 1989
4,888,018
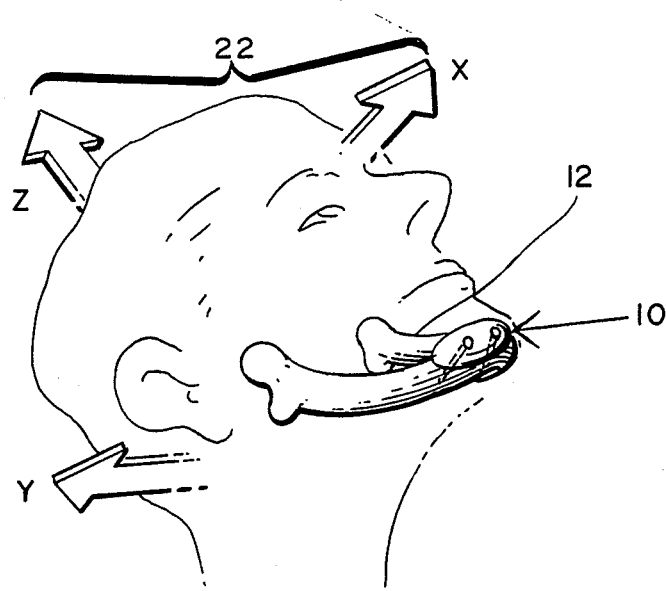
FIG.1
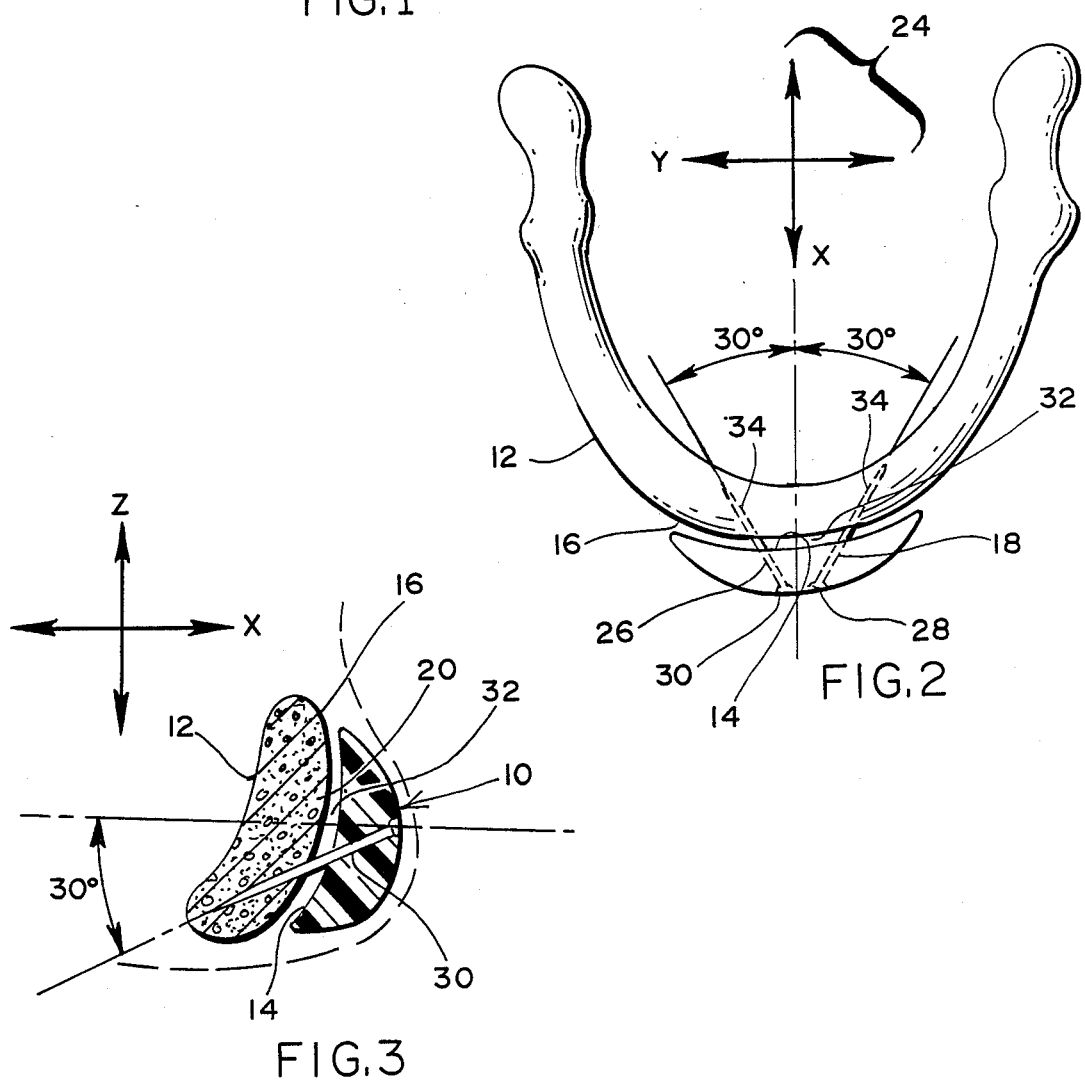
FIG.2
FIG.3

METHOD OF POSITIONING AND SECURING A CHIN IMPLANT

BACKGROUND OF THE INVENTION

The present invention is directed to a method of applying a chin implant to a human mandible.

Heretofore, chin implants of a resilient material (such as silicone) have been applied to the exposed mandible bone and retained in position by reassembled skin tissue to enclose and engage the implant. One difficulty with this procedure has been that during and after healing, such implants have been known to become mechanically displaced from the desired central location on the mandible. Also, in most instances, the pressure of the implant upon the bone has resulted in reabsorption of the bone. This process is sometimes referred to as bone reabsorption and is due to a piezoelectric effect at the bone-implant interface.

Prior art known to the inventor is limited to U.S. Pat. Nos. 3,589,0112 to Sneer; 4,344,191 (1952) to Wagner; and 4,439,152 and 4,713,077, both to Small.

None of the above, or other, prior art known to the inventor teaches the method of suspending the chin implant above the periostium of the chin in the manner taught herein.

SUMMARY OF THE INVENTION

The present invention constitutes a method of applying a chin implant to a human, the method comprising the steps of positioning a resilient preformed chin implant against an area of the chin to be enhanced, said implant having an interior radius having a curvature slightly smaller than the opposing radius of curvature of the area of the chin which is to receive the implant, As a second step, a mounting pin bore is drilled through said implant and into the periostium of said area of the chin at an outward angulation of about thirty degrees relative to a front-to-rear vertical medial plane of the face and, concurrently, at a downward angulation of about thirty degrees relative to a front-to-horizontal plane of the face taken through the area of the chin to be enhanced. A third step is defined by drilling through said implant and into said periostium a mounting pin bore having, about said front-to-rear vertical median plane, a mirror symmetry to said drilled hole described above. As a final step, there is securably inserted, through said bores, respective mounting pins which penetrate thru the periostium into the outer boney table to a depth of between two and five millimeters from the surface. Due to said difference In the radii of curvature of said inner surface of said implant and said opposing area of said chin, said two mounting pins will secure said implant at a substantially crescent-shaped offset from said chin.

It is accordingly an object of the present invention to provide a method of securably offsetting a chin implant from the area of the chin to be enhanced that will minimize the possibility of absorption of the implant material into the chin of the patient.

It is another object of the present invention to provide a method of chin implantation which will secure the implant to the chin in a manner which will minimize the potential for slippage or movement thereof.

The above and yet other objects and advantages of the present invention will become apparent from the hereinafter set forth Detailed Description of the Invention, the Drawings, and claims appended herewith.

BRIEF DESCRIPTION OF THE DRAWINGS

FIG. 1 is a side perspective, schematic view showing the positioning of the implant upon the chin and, as well, showing a Cortesian coordinate system for the purpose of defining planes of reference in the anatomy of the chin and face.

FIG. 2 is a top cross sectional view of the chin, mandible and implant taken along plane XY of FIG. 1.

FIG. 3 is a side cross sectional view taken along plane XZ in the view of FIGS. 1 and 2.

DETAILED DESCRIPTION OF THE INVENTION

In regard to the view of FIG. 1, there appears an XYZ Cartesian coordinate system which includes an XZ plane 22 which plane defines a front-to-rear vertical medial plane of the face. The system also includes a plane XY 24 which defines a front-to-rear horizontal plane at the level of the area of the chin 12 to be enhanced. See FIG. 2.

Also shown in FIG. 1 is chin implant 10 which, in a preferred embodiment, is formed of a so called soft silicone. This silicone is shaped by a so-called hard slice method.

Shown in FIGS. 2 and 3 is periostiem 20 of chin 12 and, mounting pins 28 and 30 (later described in fuller detail).

In FIG. 3 there may also be seen a substantially crescent shaped offset 32, between implant 10 and chin 12, which is achieved by virtue of the inventive method described below.

The inventive method, more particularly, comprises the steps of slideably positioning said chin implant 10, against an area of said chin 12 which is to be enhanced. Said implant exhibits an interior radius of curvature 14 which is slightly smaller than the opposing radius of curvature 16 of the area of the chin which is to receive said implant. See FIG. 2.

Thereafter, a mounting pin bore 18 (see FIG. 2) is drilled through said implant 10 and into the periostiem 20 (see FIG. 3), penetrating the periostiem to a depth of between two and five millimeters. In a preferred embodiment, the axis of bore 18 is that of an outward angulation of about 30 degrees relative to said front-to-rear vertical medial plane (the XZ plane) as is shown in FIG. 3 and, concurrently, at a downward angulation of about 30 degrees relative to said front-to-rear horizontal plane 24 (the XY plane) which is shown in FIGS. 1 and 2. It is to be noted that each of said angulations may be in the range of 15 to 45 degrees.

A third step comprises the drilling through said implant and penetrating as above defined into said periostiem a mounting pin bore 26 (see FIG. 2) having, about said front-to-rear vertical plane 22 (the XZ plane), a mirror symmetry to said mounting pin bore 18.

Thereafter there is securably inserted, through said bores 18 and 26, respective mounting pins 28 and 30 (see FIG. 2) which pins extend, as well, into the periostiem 20 (see FIG. 3) to the above noted depth 34 of between two and five millimeters As a result of the above described process and, most particularly, due to said differences in the radii of curvature 14 and 16 of said inner surface of said implant and said opposing area of said chin respectively, said two mounting pins 28 and 30 will secure the implant 10 at the substantially crescent shaped offset 32 which is shown in the views of FIGS. 1 and 3.

This offset will markedly reduce the possibility of implant displacement due to bone-implant contact, facial muscle animation, and external pressure and forces.

The offset will also markedly reduce re-absorption of the bone underlying the implant, this due to decreased implant-bone surface area contact and to elimination of the piezoelectric effect associated with bone-implant contact.

Also, it has been found that the above described angulation 28 and 30 will provide a highly stable positioning of the implant relative to the chin.

It is further noted that the X axis distance between the points of origination of said mounting pin bores 18 and 26 (see FIG. 2) is in the range of two to six millimeters. That is, the point o origination of each of said bores, from said vertical medial plane (the XZ plane) is between one and three millimeters from said plane, this equating to a distance of between two and six millimeters from the relative points of origination of said pin bores 18 and 26.

Accordingly, while there has been shown and described the preferred embodiment of the present invention, it is to be appreciated that the invention may be embodied otherwise and is herein as specifically illustrated and described and that, within the scope of such embodiments, certain changes may be made in the detail and construction of the parts without departing from the underlying idea or principles of this invention within the scope of the appended claims.

Having thus described my invention, what I claim as new, useful and non obvious and, accordingly, secure by Letters Patent of the United States is:

1. A method of applying a chin implant to a human, the method comprising the steps of:
   (a) positioning a resilient preformed chin implant against the area of an chin to be enhanced, said implant having an interior radius of curvature slightly smaller than the opposing radius of curvature of the area of said chin to be enhanced and which is to receive said implant;
   (b) drilling a mounting pin bore through said implant and into the periostium of said area of the chin to be enhanced, said drilling being at an outward angulation in the range of 15 to 45 degrees relative to a front-to-rear vertical medial plane of the face and, concurrently, at a downward angulation in the range of 15 to 45 degrees relative to a front-to-rear horizontal plane of the face;
   (c) drilling through said implant and periostium a mounting pin bore having, about said front-to-rear vertical plane, a mirror symmetry to said drilled pin bore of Step (b) above; and
   (d) securely inserting, through said bores of Steps (b) and (c) above, respective mounting pins, said pins extending thru the periostium, into the outer boney table, whereby, due to said differences in the radii of curvature of said inner surfaces of said implant and said area of the chin to be enhanced, said two mounting pins will secure said implant at a substantially crescent shaped offset from the chin.

2. The method as recited in claim 1 in which said drilling Steps (b) and (c) above comprise the steps of originating each bore between two and six millimeters apart from each other in symmetry about said vertical medial plane of the face.

3. The method as recited in claim 1 in which said drilling Steps (b) and (c) above comprise penetrating the periostium and bone to a depth of between two and five millimeters.

4. The method as recited in claim 2 in which said drilling Steps (b) and (c) above comprise the penetrating of the periostium and bone to a depth of between two and five millimeters.

5. The method as recited in claim 1 in which said drilling Step (b) comprises drilling at respective outward and downward angulations of about 30 degrees.

6. The method as recited in claim 5 in which said drilling Steps (b) and (c) above comprise the steps of originating each bore between two and six millimeters apart from each other in symmetry about said vertical medial plane of the face.

7. The method as recited in claim 6 in which said drilling Steps (b) and (c) above comprise penetrating the periostium and bone to a depth of between two and five millimeters.

* * * * *